United States Patent [19]

Zaiger et al.

[11] Patent Number: Plant 5,486

[45] Date of Patent: Jun. 4, 1985

[54] PLUM TREE '42-GA-1200'

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 509,872

[22] Filed: Jun. 30, 1983

[51] Int. Cl.[3] ..... A01H 5/00

[52] U.S. Cl. ..... Plt./38

[58] Field of Search ..... Plt./38

*Primary Examiner*—James R. Feyrer

*Attorney, Agent, or Firm*—Roger B. Webster

[57] ABSTRACT

A new and distinct variety of plum tree which is medium to large size, medium vigorous, upright, and medium dense; foliated with medium size, mostly elliptical, some oblanceolate, leaves having a serrate margin, and globose glands; flowers from plump, free buds of medium to large size and length; and is a regular and productive bearer of large, clingstone, nearly globose fruit slightly flattened at the base and apex, the fruit having bluish-red skin and yellow flesh.

1 Drawing Figure

BACKGROUND OF THE VARIETY

1. Field of the Invention

In the field of plant genetics we conduct an extensive and continuing plant breeding program including the origination and asexual reproduction of orchard trees, and of which peaches, apricots, and plums are exemplary. It was against this background of our activities that the present variety of plum tree was originated and asexually reproduced by us in an experimental orchard located at Modesto, Stanislaus County, Calif.

2. Classification of the Variety

The present new and distinct variety of plum tree is embraced by Class 38, Plants, of the U.S. Patent Office Manual of Classification.

3. Prior Varieties

Among the existent varieties of plum trees which are known to us, and mentioned herein, are Santa Rosa (unpatented), and Royal Beaut (U.S. Plant Pat. No. 3,811).

ORIGIN OF THE VARIETY

The present variety of plum tree was originated by us, in the aforesaid experimental orchard, as an open-pollinated seedling of the Royal Beaut. A substantial number of seeds of the Royal Beaut were planted, and the resultant seedlings maintained under careful and continuing observation. In maturity, one of such seedlings, and which is the present variety, evidenced certain novel and distinctive characteristics and hence was selected for asexual reproduction in contemplation of potential commercialization.

ASEXUAL REPRODUCTION OF THE VARIETY

The present variety of plum tree was asexually reproduced, in the aforesaid experimental orchard, by budding, and the reproductions ran true to the original tree and its fruit in all respects.

SUMMARY OF THE VARIETY

The present variety of plum tree is, characteristically, of medium to large size, medium vigorous, upright, and medium dense; foliated with medium size, mostly elliptical, some oblanceolate leaves having a serrate margin, and globose glands; flowers from plump, free buds of medium to large size and length; and is a regular and productive bearer of large, clingstone, nearly globose fruit slightly flattened at the base and apex, the fruit having bluish-red skin and yellow flesh.

The present variety of plum tree is further characterized by blooming with the Santa Rosa, but bears fruit which ripens approximately one week earlier.

The present variety of plum tree is still further characterized by firm flesh, clingstone fruit having a good flavor and very good storage, shipping, and eating qualities.

The present variety of plum tree is still further characterized by fruit which—throughout the tree—is nearly uniform in size, and relatively uniform in maturity.

BRIEF DESCRIPTION OF THE DRAWING

The drawing comprises illustrations, by photographic reproduction in color, of typical specimens of the foliage and fruit of the present variety of plum tree; such illustrations being of a twig with leaves, and separate fruit; one of the latter being cut in half to expose the flesh, with the stone remaining in one of the halves.

DESCRIPTION OF THE VARIETY

The botanical details of this new and distinct variety of plum tree—with color definitions (except those in common color terms) referenced to Reinhold Color Atlas by A. Kornerup and J. H. Wanscher—are as follows:

TREE

Size: Medium to large.
Vigor: Medium.
Growth: Upright.
Density: Medium.
Production: Productive.
Bearing: Regular.

TRUNK

Size: Medium.
Texture: Shaggy.

BRANCHES

Size: Medium.
Texture: Medium rough.

Color: Grayish brown to reddish brown.

LEAVES

Size: Medium.
*Length range.*—4½" To 5¾".
*Width range.*—1½" To 2".
Texture: Smooth.
Margin: Serrate.
Shape: Mostly elliptical. Some oblanceolate.
Glands:
*Number.*—Variable — 2 to 6, usually 4.
*Form.*—Globose.
*Position.*—Base of blade and distal on petiole.
Petiole:
*Average length.*—5/8".
*Average width.*—1/16".
Color:
*Upper surface.*—Dark green (28-F-6 to 28-F-7).
*Lower surface.*—Dull green (27-E-3 to 27-E-4).

FLOWER BUDS

Size: Medium to large.
Length: Medium to long.
Form: Plump. Free.

FLOWERS

Blooming period:
*Date of first bloom.*—Mar. 1, 1982.
*Date of full bloom.*—Mar. 3, 1982. Blooms with the Santa Rosa.

FRUIT

Maturity when described: Eating ripe.
Date of first picking: June 17, 1982.
Date of last picking: June 20, 1982.
Size: Large.
*Normal range.*—Axial diameter 2⅛" to 2¼".
*Normal range.*—Transverse in suture plane — 2 3/16" to 2 5/16".
Form: Usually symmetrical. Nearly globose, slightly flattened at base and apex.
Suture: Very Shallow. Nearly smooth. Extends from base to apex.
Base: Retuse.
Apex: Usually slightly depressed.
Cavity: Rounded to slightly elongated in suture plane.
*Average depth.*—¼".
*Average breadth.*—5/16".
Stem:
*Average length.*—½".
*Average width.*—3/32".

SKIN

Thickness: Medium.
Texture: Medium.

Tendency to crack: None.
Down: Wanting.
Bloom: Moderate to heavy.
Color: Bluish red (12-B-5 to 12-B-7).

FLESH

Texture: Firm. Meaty.
Ripens: Evenly.
Flavor: Mild.
Eating quality: Very good.
Color: Melon yellow (5-A-6) to chrome yellow (5-A-8). Surface area next to skin and pit cavity — orange red (8-B-8) to browinsh red (8-C-8).

STONE

Type: Clingstone.
Size:
*Average length.*—1".
*Average width.*—9/16".
*Average thickness.*—5/16".
Surface: Slightly furrowed. Ridges deeper near base.
Sides: Nearly equal.
Base: Straight.
Apex: Acuminate.
Dorsal edge: Full, with broad groove.
Ventral edge: Thin.
Color: Brownish orange (7-C-5) to light brown (7-D-6).
Tendency to split: None.

USE

Market. Local and long distance shipping.

KEEPING QUALITY

Very good.

SHIPPING QUALITY

Very good.

The plum tree and its fruit herein described may vary in slight detail due to climatic and soil conditions under which the variety may be grown; the present description being of the variety as grown in the Central Valley of California.

We claim:

1. A new and distinct variety of plum tree, substantially as illustrated and described, characerized by large, clingstone, nearly globose fruit slightly flattened at the base and apex, the fruit having bluish-red skin and firm, yellow flesh; and further characterized by blooming with the Santa Rosa but bearing fruit ripening approximately one week earlier; the fruit having a good flavor and very good storage, shipping, and eating qualities; and, throughout the tree, the fruit being nearly uniform in size and relatively uniform in maturity.

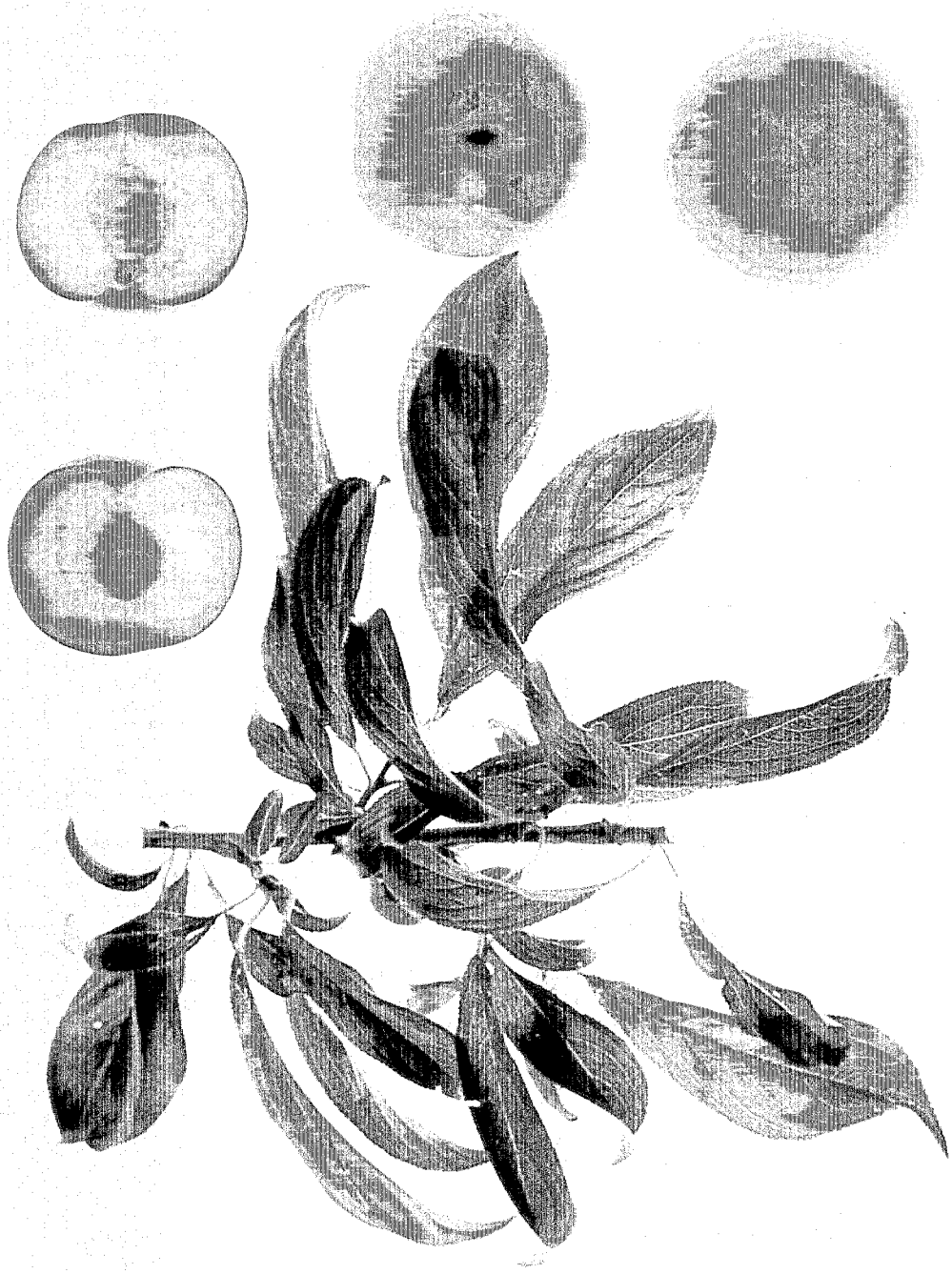

* * * * *